(12) United States Patent
Wright et al.

(10) Patent No.: US 7,993,432 B2
(45) Date of Patent: Aug. 9, 2011

(54) AIR COLLECTOR WITH FUNCTIONALIZED ION EXCHANGE MEMBRANE FOR CAPTURING AMBIENT $CO_2$

(75) Inventors: Allen B. Wright, Tucson, AZ (US); Eddy J. Peters, Tucson, AZ (US)

(73) Assignee: Kilimanjaro Energy, Inc., Waukesha, WI (US)

( * ) Notice: Subject to any disclaimer, the term of this patent is extended or adjusted under 35 U.S.C. 154(b) by 561 days.

(21) Appl. No.: 11/683,824

(22) Filed: Mar. 8, 2007

(65) Prior Publication Data

US 2007/0217982 A1    Sep. 20, 2007

Related U.S. Application Data

(60) Provisional application No. 60/780,466, filed on Mar. 8, 2006, provisional application No. 60/780,467, filed on Mar. 8, 2006.

(51) Int. Cl.
*B01D 53/02* (2006.01)
(52) U.S. Cl. .......................................................... 95/139
(58) Field of Classification Search .................... 96/236, 96/139
See application file for complete search history.

(56) References Cited

U.S. PATENT DOCUMENTS

| | | |
|---|---|---|
| 1,031,799 A | 9/1912 | MacKay |
| 3,466,138 A | 9/1969 | Speigler et al. ................. 49/13 |
| 3,498,026 A | 3/1970 | Messinger et al. .............. 55/73 |
| 3,627,478 A | 12/1971 | Tepper ........................ 423/230 |
| 3,712,025 A | 1/1973 | Wallace |
| 3,727,375 A | 4/1973 | Wallace |
| 3,833,710 A | 9/1974 | Deschamps et al. |
| 3,865,924 A | 2/1975 | Gidaspow et al. ............ 423/230 |
| 4,047,894 A | 9/1977 | Kuhl .............................. 23/284 |
| 4,197,421 A | 4/1980 | Steinberg ..................... 585/733 |
| 4,528,248 A | 7/1985 | Galbraith ....................... 429/72 |
| 4,566,221 A | 1/1986 | Kossin ........................ 47/41.12 |
| 4,711,645 A | 12/1987 | Kumar ............................ 55/26 |
| 5,070,664 A | 12/1991 | Groh et al. ..................... 52/177 |
| 5,344,627 A | 9/1994 | Fujii et al. .................... 423/220 |
| 5,414,957 A | 5/1995 | Kenney ....................... 47/41.12 |
| 5,454,189 A | 10/1995 | Graham et al. .............. 47/41.12 |
| 5,682,709 A | 11/1997 | Erickson ....................... 47/58.1 |
| 5,711,770 A * | 1/1998 | Malina ........................ 48/197 R |
| 5,779,767 A | 7/1998 | Golden et al. .................... 95/96 |
| 5,797,979 A | 8/1998 | Quinn ............................. 95/97 |
| 5,887,547 A | 3/1999 | Caveny et al. ................ 119/174 |
| 5,914,455 A | 6/1999 | Jain et al. ......................... 95/96 |
| 5,917,136 A | 6/1999 | Gaffney et al. ................... 95/98 |

(Continued)

FOREIGN PATENT DOCUMENTS
DE          19521678          6/1995
(Continued)

OTHER PUBLICATIONS

Office Action dated Sep. 11, 2009, U.S. Appl. No. 11/209,962, (16 pgs).

(Continued)

*Primary Examiner* — Duane Smith
*Assistant Examiner* — Tiffany N Palmer
(74) *Attorney, Agent, or Firm* — Hayes Soloway P.C.

(57) ABSTRACT

An apparatus for capture of $CO_2$ from the atmosphere comprising an anion exchange material formed in a matrix exposed to a flow of the air.

7 Claims, 5 Drawing Sheets

U.S. PATENT DOCUMENTS

| | | | | |
|---|---|---|---|---|
| 5,972,080 | A | 10/1999 | Nagata | 96/13 |
| 5,980,611 | A | 11/1999 | Kumar et al. | 95/101 |
| 6,136,075 | A | 10/2000 | Bragg et al. | 96/135 |
| 6,180,012 | B1 | 1/2001 | Rongved | 210/717 |
| 6,237,284 | B1 | 5/2001 | Erickson | 47/58.1 |
| 6,279,576 | B1* | 8/2001 | Lambert | 128/205.28 |
| 6,334,886 | B1 | 1/2002 | Barnes et al. | |
| 6,503,957 | B1 | 1/2003 | Bernatowicz et al. | 521/27 |
| 6,582,498 | B1 | 6/2003 | Sass et al. | 95/211 |
| 6,617,014 | B1 | 9/2003 | Thomson | 428/304.4 |
| 6,716,888 | B2 | 4/2004 | Bernatowicz et al. | 521/27 |
| 6,890,497 | B2 | 5/2005 | Rau et al. | 423/220 |
| 7,132,090 | B2* | 11/2006 | Dziedzic et al. | 423/230 |
| 7,343,341 | B2 | 3/2008 | Sandor et al. | 705/37 |
| 7,364,608 | B2 | 4/2008 | Tanahashi et al. | 96/108 |
| 7,384,621 | B2 | 6/2008 | Stevens et al. | 423/650 |
| 7,415,418 | B2 | 8/2008 | Zimmerman | 705/1 |
| 7,420,004 | B2* | 9/2008 | Hardy et al. | 518/704 |
| 7,699,909 | B2 | 4/2010 | Lackner et al. | 95/236 |
| 2001/0004895 | A1 | 6/2001 | Preiss | 128/205.28 |
| 2001/0009124 | A1 | 7/2001 | Suzuki et al. | 95/113 |
| 2002/0083833 | A1 | 7/2002 | Nalette et al. | 95/139 |
| 2003/0145726 | A1 | 8/2003 | Gueret et al. | 95/96 |
| 2003/0167692 | A1 | 9/2003 | Jewell et al. | 48/197 |
| 2004/0031424 | A1 | 2/2004 | Pope | 110/230 |
| 2004/0069144 | A1 | 4/2004 | Wegeng et al. | 95/106 |
| 2004/0103831 | A1 | 6/2004 | Pope | 110/341 |
| 2004/0134353 | A1 | 7/2004 | Gillingham et al. | |
| 2004/0213705 | A1 | 10/2004 | Blencoe et al. | 422/129 |
| 2004/0219090 | A1* | 11/2004 | Dziedzic et al. | 423/437.1 |
| 2005/0011770 | A1 | 1/2005 | Katsuyoshi et al. | |
| 2005/0092176 | A1 | 5/2005 | Ding et al. | 95/90 |
| 2005/0204915 | A1 | 9/2005 | Sammons et al. | |
| 2006/0013963 | A1 | 1/2006 | Thomson | 427/487 |
| 2006/0042209 | A1 | 3/2006 | Dallas et al. | 55/524 |
| 2006/0186562 | A1 | 8/2006 | Wright et al. | |
| 2006/0249020 | A1 | 11/2006 | Tonkovich et al. | |
| 2007/0004023 | A1 | 1/2007 | Tranchtenberg | |
| 2007/0199448 | A1* | 8/2007 | Yates et al. | 95/139 |
| 2008/0025893 | A1 | 1/2008 | Asprion et al. | 423/228 |
| 2008/0031801 | A1 | 2/2008 | Lackner et al. | 423/438 |

FOREIGN PATENT DOCUMENTS

| | | |
|---|---|---|
| DE | 197 27 295 | 1/1999 |
| DE | 20001385 | 1/2000 |
| EP | 0020055 | 5/1980 |
| EP | 0254137 | 1/1988 |
| FR | 2.029.424 | 10/1970 |
| GB | 1 031 799 | 2/1963 |
| GB | 1 296 889 | 11/1972 |
| JP | 58-122022 | 7/1983 |
| JP | 63 12323 | 1/1988 |
| JP | 63 12324 | 1/1988 |
| JP | 63-69525 | 3/1988 |
| JP | 63-69527 | 3/1988 |
| JP | 1-208310 | 8/1989 |
| JP | 2004-261757 | 9/2004 |
| WO | WO 98/16296 | 4/1998 |
| WO | WO 1998/17388 | 4/1998 |
| WO | WO 2000/050154 | 8/2000 |
| WO | WO 00/76633 | 12/2000 |
| WO | WO 2001/021269 | 3/2001 |
| WO | WO 2005/108297 | 11/2005 |
| WO | WO 2006/009600 | 1/2006 |
| WO | WO 2007/016271 | 2/2007 |

OTHER PUBLICATIONS

EP Extended Search Report, dated, Jun. 22, 2010, (12 pgs).
Lackner, at al., "Free-Market Approaches to Controlling Carbon Dioxide Emissions to the Atmosphere: A Discussion of the scientific basis", Los Alamost National Laboratory (Lackner and bock) & Harvard University (Wilson), pp. 1-16, 1999.
Lackner, Klaus S., "Can Fossil Carbon Fuel the 21st Century?", International Geology Review, vol. 44, 2002, pp. 1122-1133.
"Extraction of Carbon Dioxide from the Atmosphere Through Engineered Chimical Sinkage", Dubey et al., Fuel Chemistry Division Preprints, 2001, pp. 1-4.
"Extracting CO2 from the Air", Lackner presentation, 12 pgs, 1999.
"Carbon Dioxide Extraction From Air: Is It an Option?", Lackner et al., Proceedings of the 24th Annual Technical Conference on Coal Utilization and Fuel Systems, Mar. 8-11, 1999, pp. 885-896.
"Compensation of Atmospheric CO2 Buildup Through Engineered Chemical Sinkage", Elliott et al., pp. 1-8, 2001.
"Capturing Carbon Dioxide From Air", Lackner et al., pp. 1-15, 1999.
"The Case for Carbon Dioxide Extraction from Air", Lackner et al., Sourcebook, Sep. 1999, vol. 57, No. 9, pp. 6-10.
"An Industrial Sized Unit" Drawing and specification, 2005.
"Carbon Dioxide Extraction from Air", Lackner et al., Arguments pp. 1-5, 1999.
"New Findings May Redefine Renewable Energy Debate", Bituin, found at http://www.dailycal.org/article.php?id=8539, 2002.
"Imagine No Restrictions on Fossil-Fuel Usage and No Global Warming!", Rickman, found at http://www.lanl.gov/news/releases/archive/02-028.shtml, 2002.
"In the Lab", Jason Hensel, found at www.eponline.com, 2002.
"Americans Believe in Global Warming . . . and Psychic Powers, Astrology, and UFO's", S. Fred Singer, found at http://heartland.org/, 2002.
"Science for Sustainability: From Capturing Carbon Dioxide From Air to Environmental Impact of a Hydrogen Economy", Dubey, found at http://www.mbari.org/seminars/2003/spring2003/apr2dubey.html.
"New Solutions to Oil Problems" Whitley Strieber's Unknown Country, 2002, found at http://www.unknowncountry.com/news/print.phtml?id=1467.
"Chimical Extraction of Carbon Dioxide from Air to Sustain Fossil Energy by Avoiding Climate Change", Dubey et al., 2nd Annual Conference on Carbon Sequestration, 2003.
"Researchers Explore Extracting CO2 Directly From Air" found at http://www.earthvision.net/ColdFuston/News_Page1.cfm?NewsID=20309, 2006.
Abstracts of Eos. Trans. AGU, 83(19), Spring Meeting 2002, 3 pgs.
Abstracts of Eos. Trans. AGU, 83(47), Fall Meeting 2002, 3 pgs.
"Written Public Comments on the Strategic Plan for the U.S. Climate Change Science Program, General Comments", 2003, pp. 1-160.
Environment & Climate News, vol. 5, No. 7. Aug. 2002, 20 pgs.
"Carbon Sequestration Could be Employed Today to Help Alleviate Greenhouse Emissions" found at http://www.earthinstitute.columbia.edu/news/2003/story06-25-03b.html.
"CO2 Capture from the Air: Technology Assessment and Implications for Climate Policy", Keith et al., pp. 1-6, 2006.
Resume of David Keith, Spring 2005, 8 pgs.
"Climate Strategy with CO2 Capture From the Air", Keith et al., found at http://ideas.repec.org/p/hal/papers/halshs-00003926_v1.html, 2005.
"Information About: David Keith" found at http://ideas.repec.org/e/pke74.html, 2005.
"Climate Strategy with CO2 Capture from the Air" Keith et al., Mar. 31, 2005, pp. 1-43.
Abstracts of Eos. Trans. AGU, 82(47), Fall Meeting 2001, 3 pgs.
"The Carrot or the Stick: How to Build a Technology-Friendly Climate Policy in Canada" Presentation by David Keith, Climate Change Central Apr. 15, 2005, pp. 1-32.
Information on David Keith found at http://www.ucalgary.ca/-keith/, 2005.
Chinese Office Action dated Dec. 3, 2010 with English translation (8 pages).
Office Action dated Nov. 10, 2010 in U.S. Appl. No. 11/996615.
Office Action dated Nov. 9, 2010 in U.S. Appl. No. 12/638717.
Official Action dated Mar. 28, 2011 in U.S. Appl. No. 12/389,213.
Official Action issued in Applicants' counterpart Russian Patent Application Serial No. 2008139902 dated Feb. 4, 2011.

* cited by examiner

SPIRAL WOUND
DISC

CONCENTRIC
LAYERS DISC

VARIABLE
THICKNESS

INTEGRATING $CO_2$ CAPTURE FROM THE AIR WITH OTHER INDUSTRIAL PROCESSES FOR SEQUESTRATION

AIR COLLECTOR WITH FUNCTIONALIZED ION EXCHANGE MEMBRANE FOR CAPTURING AMBIENT $CO_2$

CROSS REFERENCE TO RELATED APPLICATIONS

The present application claims priority from U.S. Provisional Application Ser. No. 60/780,466 and 60/780,467, both filed Mar. 8, 2006, the contents of which are incorporated herein by reference.

BACKGROUND OF THE INVENTION

The present invention in one aspect relates to removal of selected gases from air. The invention has particular utility for the extraction of carbon dioxide ($CO_2$) from air and will be described in connection with such utilities, although other utilities are contemplated, including the sequestration of other gases including $NO_x$ and $SO_2$.

There is compelling evidence to suggest that there is a strong correlation between the sharply increasing levels of atmospheric $CO_2$ with a commensurate increase in global surface temperatures. This effect is commonly known as Global Warming. Of the various sources of the $CO_2$ emissions, there are a vast number of small, widely distributed emitters that are impractical to mitigate at the source. Additionally, large scale emitters such as hydrocarbon-fueled power plants are not fully protected from exhausting $CO_2$ into the atmosphere. Combined, these major sources, as well as others, have lead to the creation of a sharply increasing rate of atmospheric $CO_2$ concentration. Until all emitters are corrected at their source, other technologies are required to capture the increasing, albeit relatively low, background levels of atmospheric $CO_2$. Efforts are underway to augment existing emissions reducing technologies as well as the development of new and novel techniques for the direct capture of ambient $CO_2$. These efforts require methodologies to manage the resulting concentrated waste streams of $CO_2$ in such a manner as to prevent its reintroduction to the atmosphere.

The production of $CO_2$ occurs in a variety of industrial applications such as the generation of electricity power plants from coal and in the use of hydrocarbons that are typically the main components of fuels that are combusted in combustion devices, such as engines. Exhaust gas discharged from such combustion devices contains $CO_2$ gas, which at present is simply released to the atmosphere. However, as greenhouse gas concerns mount, $CO_2$ emissions from all sources will have to be curtailed. For mobile sources the best option is likely to be the collection of $CO_2$ directly from the air rather than from the mobile combustion device in a car or an airplane. The advantage of removing $CO_2$ from air is that it eliminates the need for storing $CO_2$ on the mobile device.

Extracting carbon dioxide ($CO_2$) from ambient air would make it possible to use carbon-based fuels and deal with the associated greenhouse gas emissions after the fact. Since $CO_2$ is neither poisonous nor harmful in parts per million quantities, but creates environmental problems simply by accumulating in the atmosphere, it is possible to remove $CO_2$ from air in order to compensate for equally sized emissions elsewhere and at different times.

Various methods and apparatus have been developed for removing $CO_2$ from air. In one prior art method, air is washed with a sorbent such as an alkaline solution in tanks filled with what are referred to as Raschig rings that maximize the mixing of the gas and liquid. The $CO_2$ reacts with and is captured by the sorbent. For the elimination of small amounts of $CO_2$, gel absorbers also have been used. Although these methods are efficient in removing $CO_2$, they have a serious disadvantage in that for them to efficiently remove carbon dioxide from the air; the air must be driven past the sorbent at fairly high pressures. The most daunting challenge for any technology to scrub significant amounts of low concentration $CO_2$ from the air is to process vast amounts of air and concentrating the $CO_2$ with an energy consumption less than that that originally generated the $CO_2$. Relatively high pressure losses occur during the washing process resulting in a large expense of energy necessary to compress the air. This additional energy used in compressing the air can have an unfavorable effect with regard to the overall carbon dioxide balance of the process, as the energy required for increasing the air pressure may produce its own $CO_2$ that may exceed the amount captured negating the value of the process.

Such prior art methods result in the inefficient capture of $CO_2$ from air because these processes heat or cool the air, or change the pressure of the air by substantial amounts. As a result, the net loss in $CO_2$ is negligible as the cleaning process may introduce $CO_2$ into the atmosphere as a byproduct of the generation of electricity used to power the process.

The present invention in one aspect provides an improvement over prior art systems for removal of $CO_2$ from air by the utilization of solid phase anion exchange membranes for the direct capture of $CO_2$ and other acid gases such as $NO_x$ and $SO_2$ from air. Specifically, this invention provides practical physical configurations of the active element, processes for the manufacture of the active element and configurations options of an air collector device to facilitate the direct capture of $CO_2$ and other acid gases from the air based on solid phase, anion exchange materials.

SUMMARY OF THE INVENTION

This invention in one aspect provides practical physical configurations of active air contacting elements, processes for the manufacture of the active elements and configurations options of an air collector device to facilitate the direct capture of $CO_2$ and other acid gases from the air based on solid phase, anion exchange materials.

The air capture device in accordance with the present invention constitutes a front-end component of a larger system designed to capture low concentration ambient $CO_2$, chemically remove the captured $CO_2$ from the air capture device, concentrate the $CO_2$ for subsequent permanent disposal, reconstitute the process chemicals and reactivate the $CO_2$ capture materials in preparation for the next capture cycle.

The air capture device utilizes a functionalized anion exchange polymer that is formed to provide a relatively large surface area which allows for air flow with minimum resistance. In one embodiment the anion exchange polymer takes the form of an open matrix or unordered mesh of "noodle-like" strands, e.g., similar to those found in evaporative or humidifier pads. Alternatively, the anion exchange polymer is formed into cells or coated on surfaces of a support material formed into cells that provides certain critical capture performance requirements.

In our co-pending PCT Application Serial No. PCT/US06/029238, filed Jul. 28, 2006, we describe specific requirements for the chemical performance of the solid phase ion exchange material. This application in one aspect addresses mechanical configurations and air-side performance enhancements to ensure that the low energy needs of the overall system are met while ensuring a robust design with repeatable air capture performance. In another aspect, this application describes an integrated system for reforming $CO_2$ into other molecules that will permanently prevent the reintroduction of the captured $CO_2$ into the atmosphere.

BRIEF DESCRIPTION OF THE DRAWINGS

Further features and advantages of the present invention will be seen from the following detailed description, taken in conjunction with the accompanying drawings, wherein FIG. 1 a flow diagram illustrating a capture of $CO_2$ from the air.

DETAILED DESCRIPTION OF PREFERRED EMBODIMENTS

Figure 1:
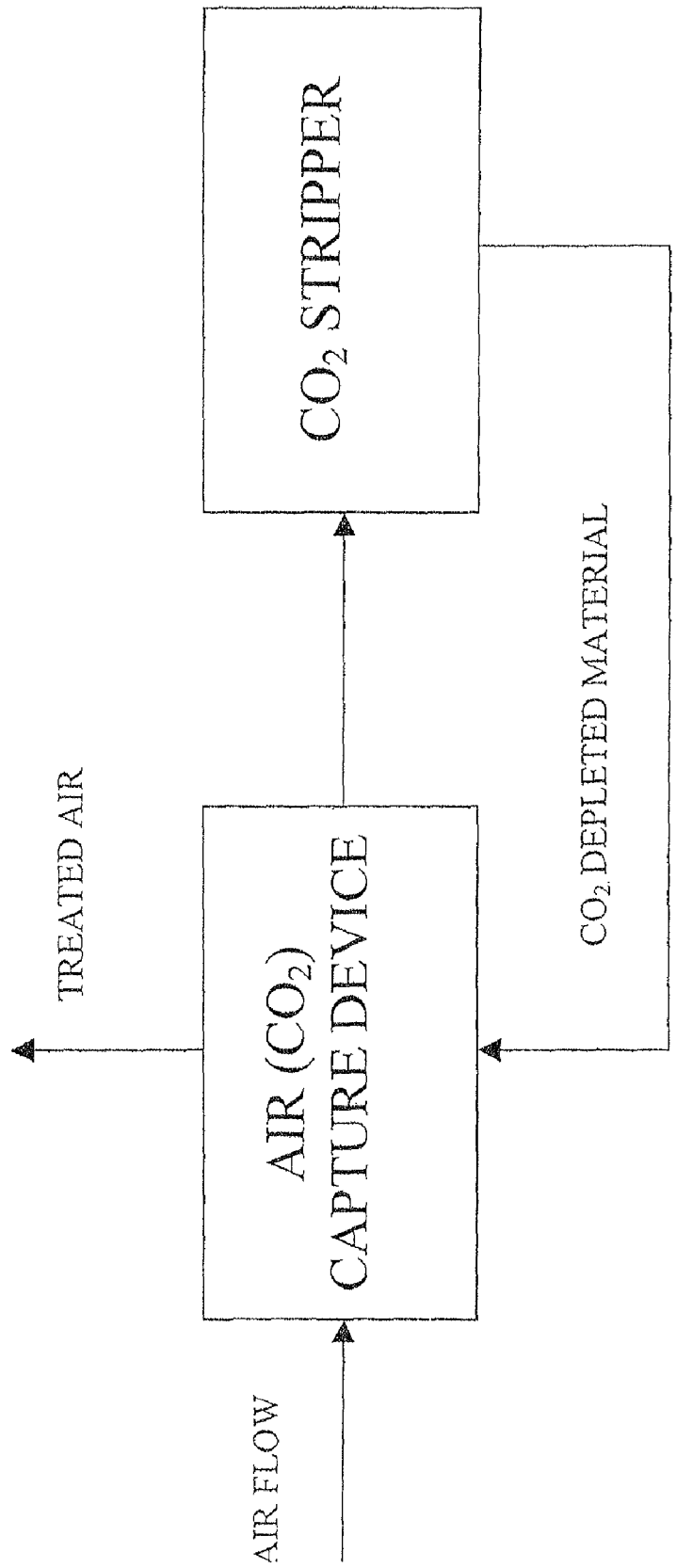

One goal of the air capture device of the present invention is to present a maximum amount of surface area of the solid phase ion exchange material per unit volume to a high volume flow rate, low pressure air stream while minimizing air pressure drop across the device.

Preferably, the air capture device also is configured to ensure as complete as possible penetration and thorough liquid contact of all surfaces with a sorbent chemical to remove the captured $CO_2$ and to reactivate the membrane surfaces.

In operation, the air capture device will be exposed to a stream of air for a given period of time until, through known performance characterization, it will be necessary to remove the captured carbon-bearing molecules and reactivate the solid phase anion exchange materials. The solid phase anion exchange materials will then be treated, for example with a sorbent chemical, e.g. through liquid bath immersion or spray, to remove the carbon-bearing molecules and reactivate the solid phase anion exchange materials. Once drained, the air capture device can be reintroduced to the air stream.

Preferably, the air capture device is oriented to the air stream with its major feature or face substantially perpendicular to the air stream flow path. The face is penetrated by a matrix of passages that are parallel with the principal axis of the air stream and that pass completely through the bulk of the air capture device.

As stated previously, the amount of energy expended by the air capture and cleaning process to capture and concentrate atmospheric $CO_2$ must be minimized. To be viable, the process should introduce less $CO_2$ into the atmosphere as a byproduct of the generation of electricity used to power the process than that amount of $CO_2$ that is captured. This impacts the configuration of the air capture device, specifically its aerodynamic impedance to the incoming process air stream.

The ideal arrangement of the device will be to utilize available wind driven airflow without fan assistance; however, the case for fan assisted airflow must also be considered. Given that a known amount of air must be processed to extract a known amount of $CO_2$ (on the order of 10,000 units of air to every unit of $CO_2$) and that the impedance presented by the air capture device will have a direct influence on the fan input power, it is necessary to minimize air-side pressure drop through the device. This may be achieved through the design of low pressure drop features that communicate air from inlet to the outlet faces of the air capture device with low flow resistance.

In competition with the above requirement, another critical criterion requires the maximization of the specific active surface area of the device. Expressed as the unit active area per unit volume of the bulk mass of the device, one goal of the present invention is to limit the overall physical size of the air capture device. The concern arises from experimentally derived $CO_2$ capture flux values for the ion exchange material under consideration. Although relative to other $CO_2$ capture methodologies, it performs very well, and flux values are quite low. Specifically, we have demonstrated average capture fluxes from 2 to 6E-5 moles $CO_2/m^2/sec$. This has a significant impact on the amount of surface area of active material necessary to achieve practical capture quantities. For example, at 2E-5 moles $CO_2/m^2/sec$ with the goal of capturing 1 tonne of $CO_2/day$, the device would be required to expose 13,150 $m^2$ of membrane to the air stream. Thus, the device needs to be configured with a high specific active surface area matrix to achieve a practical device without severe limitations on its location owing to the collector size.

A third criterion is the ability of the structural matrix to be thoroughly wetted by the sorbent chemistry necessary to remove the captured $CO_2$ and to refresh the active material. Commensurate with its ability to be easily and thoroughly wetted is its ability to completely drain in preparation for the next processing cycle.

A fourth criterion requires that the structural matrix be configured to present a robust, uniform and dimensionally stable form. This is necessary given the following factors:

1. Firstly, the material may undergo significant dimensional variations owing to expansion and contraction processes between the wet and dry states. The fabrication of the matrix must provide robust joints between subcomponents to withstand the repeating strain over years of cycling without tear or rupture.
2. The design of the internal features must accommodate the expansion and contraction while maintaining dimensional stability. This is necessary in order to avoid localized and/or gross reductions in cross-sectional area as presented to the air stream which would lead to a reduction in the exposed active membrane.

Very high specific active surface area will compete, however, with the requirements for low pressure drop, this arising from the fact that high surface area to volume efficiencies are achieved with very small internal features or passages. Additionally, very small internal features may also compromise air flow by causing air stagnation in these features below a characteristic critical air flow.

Thus, the final design and configuration will be an optimization of pressure drop, specific active surface area and overall collector size. This will also be influenced by practical manufacturing processes necessary to make a robust and cost effective device.

Design and Configuration of Active Element
 a. Requirements Overview

The air capture device of the present invention comprises a field or matrix of active elements or features that communicate directly between two opposing faces in such a manner as to minimize energy loss owing to aerodynamic forces arising from airflow through these features. In one embodiment of the invention, the active elements or features take the form of an open matrix or unordered mesh of "noodle-like" strands, similar to those found in evaporative or humidifier pads. In another embodiment of the invention the active elements or features are comprised of repeating shapes such as, but not limited to, regular and irregular polygons that may be of varying sizes and shapes occupying the complete matrix. The shape, size and distribution may vary over the entire matrix in order to optimize the airflow characteristics and pressure drop distribution to achieve the desired capture kinetics and structural performance criteria noted previously.

b. Physical and Performance Attributes

The smaller the cross-sectional area of a given feature, the higher the specific area of a unit volume of the matrix, i.e., specific area being the ratio of area to volume. For example for a matrix of rows of equilateral triangles, 5 mm on each side, each row separated by a planar sheet would have a specific area of approximately 1200 $m^2/m^3$. A matrix of 10 mm equilateral triangles would present a specific area of approximately 600 $m^2/m^3$.

The trade-off of a small feature size is that with the air-side aerodynamic characteristics of turbulence and pressure drop. For a given airflow, as the cross-sectional area of the feature is reduced, the turbulence and pressure drop along the air path length will increase. To a limited extent, turbulence is desirable to ensure good $CO_2$ capture kinetics with a solid phase anion exchange material. However, a cost for higher turbulence and commensurate pressure drop though is the higher energy required to move the air through the air capture device. For a given surface roughness of the solid phase anion exchange material in contact with the process air, the significant performance trade-off variables are feature cross-sectional area and uniformity, flow path length, air velocity flux at the face of the matrix and $CO_2$ capture kinetic response of the solid phase anion exchange material.

Overlaying these performance trade-off issues are those related to the manufacturing and assembly of the features and the matrix. The manufacturing process necessary to create the small features while ensuring a robust and consistent assembly will be reflective of the starting raw materials. The two most common forms of solid phase anion exchange materials are thermoplastic sheet and beads. The practicality of forming small features will be driven by available processes and practices given these materials. There may be certain feature sizes, below which the manufacturing process may need to change potentially resulting in higher unit costs.

c. Configuration Options

At the most discrete level, the repeating feature would be comprised of repeating shapes such as, but not limited to, regular and irregular polygons that may be of varying sizes and shapes comprising the complete matrix. The selection of shape would be influenced, in part, by the specific area requirements and manufacturability. Additionally, the overall configuration of the air capture device may dictate more than one feature shape in order to maximize exposure to the air stream and adjust for differential air velocity fluxes. Potential shapes include, but are not limited to, isosceles and equilateral triangles, trapezoids, squares, rectangles, other regular and irregular polygons. See, e.g. FIGS. 2a-2f. The shaped anion exchange material may be formed from sheets of anion exchange material such as functionalized polystyrene or the like, or comprise sheets of inert substrate material coated with anion exchange material. Alternatively, and in a preferred embodiment of the invention, the anion exchange material comprises "noodle-like" 1 mm thick by 1 mm wide strands formed by slitting commercially available anion exchange membrane material. One currently preferred material is an anion exchange membrane material available from SnowPure, LLC, San Clemente, Calif. The manufacturer describes these membrane materials as comprising crushed anionic exchange resin mixed in a polypropylene matrix and extruded as a sheet according to the teachings of U.S. Pat. Nos. 6,503,957 and 6,716,888. The "noodles" or strands are formed by slitting 1 mm thick sheets of SnowPure anion exchange material into 1 mm wide "noodles" or strands. (See FIGS. 2h-2h).

Figure 3A:
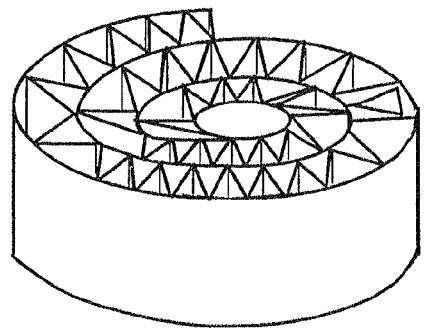
FIGS. 3a, 3b and 4 are perspective views illustrating various embodiments of air capture media in accordance with the present invention.
Figure 3B:
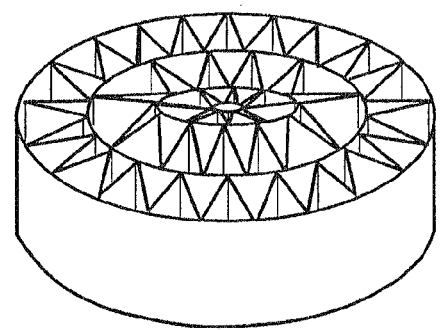

In accordance with one embodiment of the invention, an air capture device may be formed in a substantially circular shape and constant thickness shape, i.e., a disc, using a matrix of polygons which follow a spiral pattern to take advantage of a continuous strip of corrugated solid phase anion exchange material that is as wide as the air capture device is thick. See, e.g. FIGS. 3a and 3b. The unit would be wound with a continuous corrugated layer and a co-joined planar layer until the desired diameter is achieved. An alternative to this configuration would be discrete increasingly larger diameter annular segments of corrugated solid phase anion exchange material and planar sheet subassemblies that would fit snugly together until the desired diameter of the air capture device is achieved.

Figure 4:
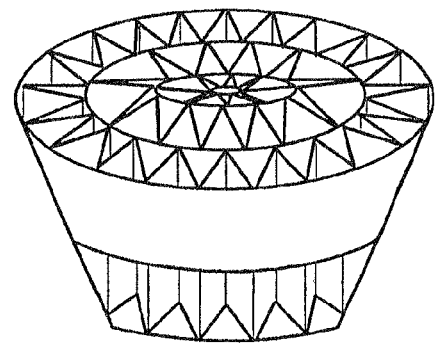

A variant of the above example would have a disc of variable thickness. See, e.g. FIG. 4. This may be desirable in the presence of a non-uniform air flux field in order to ensure uniform capture and/or aerodynamic performance throughout the mass of the air capture device.

Figure 5:
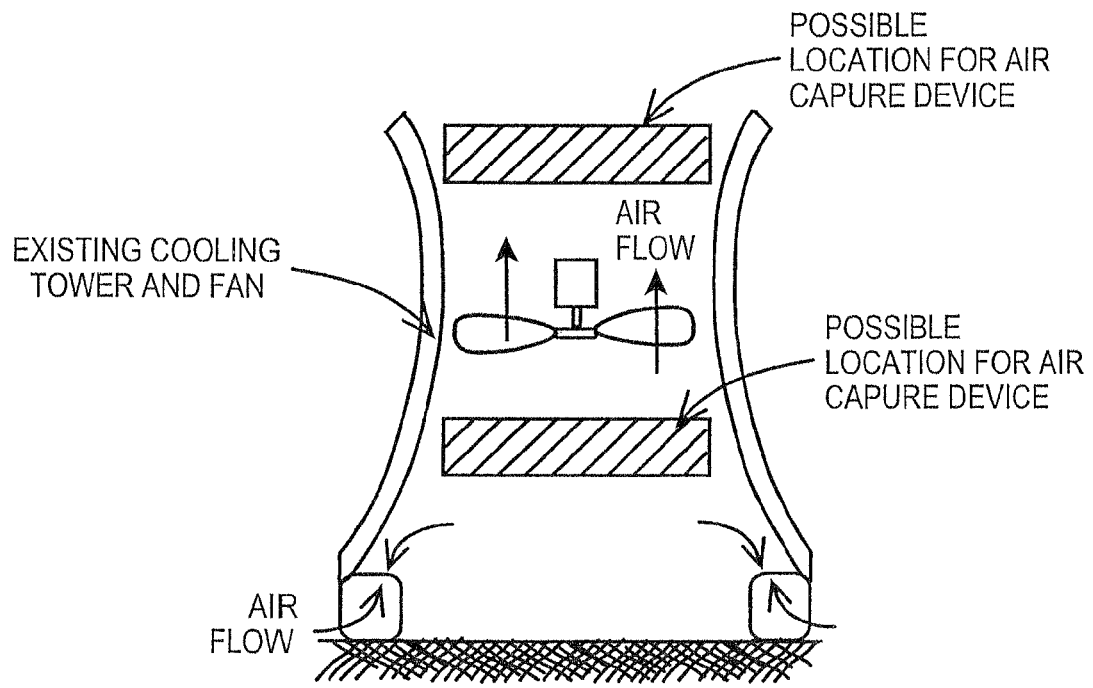
FIG. 5 schematically illustrates air capture media installed in a cooling tower in accordance with the present invention.

One advantage of the circular cross-section would be to match the geometry of the air capture device to a cooling tower such as an up-draft cooling tower which is circular in cross-section as well. See, e.g. FIG. 5. This circular feature also lends itself to retrofit applications of existing cooling tower installations.

Figure 6:
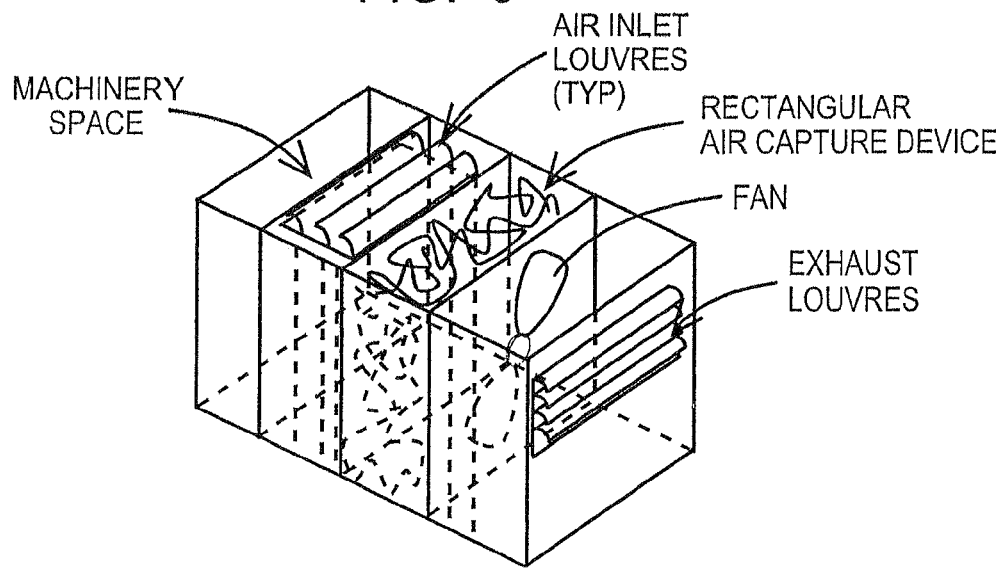
FIG. 6 is a schematic view showing air capture media installed in an exhaust system in accordance with the present invention.

Another configuration for the air capture device would be substantially rectangular, e.g., as shown in FIG. 6. The matrix would consist of a field of regular, repeating polygons set in rows or columns separated from each other by planar sheets. An alternative arrangement would include substantially a field of regular polygons with discretely placed regions of alternate shapes, patterns and/or sizes to optimize the $CO_2$ capture kinetics and aerodynamic performance throughout the mass of the air capture device. One advantage to this configuration is that it lends itself to an installation into a standard shipping container facilitating the development of a stand-alone, integrated and self-contained device that is readily shipped via the existing intermodal transportation infrastructure.

In all the configurations previously discussed, a significant advantage to the matrix arrangement of the polygon-based features is its inherent structural stability and strength. In the planar sheet form, the solid phase anion exchange material has no practical structure for stability and low specific area and in the bead form, the solid phase anion exchange material has high pressure drop and requires external containment structures. A fabricated matrix of solid phase anion exchange material or a substrate coated with an anion exchange material creates a space frame structure similar to that used in aircraft floors and automobile bodies. In these applications, the space frame allows the designer to create a very stiff, strong and stable structure that is light weight with a very high strength to weight ratio. An example in nature of a similar matrix of regular polygons, fabricated from light weight material that yields a highly stable and strong 3-dimensional structure is the beehive.

Overview of Manufacturing Processes a. Overview and Requirements

Common ion exchange resins are made up of a polystyrene or cellulose based backbone which is subsequently functionalized Laminated) into the anionic form usually via chloromethalation.

The manufacturing processes available to assemble the proposed matrix structure can take advantage of the formability offered by the polystyrene thermoplastic. Broadly, there are two paths open to the fabrication process. The first involves the formation of an assembled matrix or mesh prior to its activation or functionalization. This allows the fabricator the flexibility of apply a broad selection of mature plastics fabrication processes to manufacture the air capture matrix that would otherwise damage or destroy a functionally treated material. The primary concern is that the temperatures involved in melting polystyrene exceed the upper limit tolerance of the functionalized material.

The other fabrication path involves the use of pre-treated or functionalized material. This provides the option of working with pre-existing solid phase anion exchange materials albeit with some limitations to the processing conditions in order to preserve the ionic capabilities of the material. The limitation arises from the relatively low temperature tolerance of the functional amine groups on the material. The upper temperature limit is in the range of 100 to 140° C., well below the processing temperature necessary to fuse the thermoplastic material. Polystyrene has a $T_g$ or glass transition temperature of approximately 100° C. and a melting point around 240° C. As a result, the material can be worked or formed near the upper safe limit for the functionalized material without melting the material which would destroy the functionality.

Experimentation with thermoplastic solid phase anion exchange materials has shown that highly localized fusion bonding processes, such as spot welding, may be for the assembly of the matrices as the heat-affected zone is highly localized limiting the amount of functionality that is removed by this processes. This process does not significantly impact the bulk performance of the solid phase anion exchange materials.

b. Forming of Features and Assembly of Matrix

Selection of the shape of the features will be influenced, in part, by the manufacturing processes available. For example, the choice of a simple polygon, such as a triangle, lends itself to some simple forming processes. Starting with a continuous sheet of either pre- or post-functionalized polystyrene in roll form, a continuous forming operation of creating a corrugation can be achieved by passing the sheet between two heated and matched contoured rollers. The precisely spaced rollers will capture the polystyrene, heat the material to its glass transition temperature and impart the triangular shape. As the corrugated sheet exits the rollers, they are allowed to cool to ensure the shape takes a permanent set. For shapes that feature sharp bends or that require more severe processing, the post-functionalized material may be more suitable to allow for higher temperature processing.

Another forming processes that yields similar results as in the above example but produces formed sheets on a discrete basis, would be to press planar sheets between two heated and contoured platens under pressure. As before, the shape's features may dictate the forming temperatures and therefore the selection of pre- or post-functionalized material.

Another forming process takes advantage of the existing technologies applied to the manufacturing of plastic parts. Specifically, polystyrene can be heated and extruded or injection molded to form complex shapes. Whether discrete parts or continuously cast shapes, the final product would then be functionalized after formation.

Yet another forming process involves the creation of a polystyrene foam material. With the addition of blow agents, an open-cell foam material would be created, the material cut into shape, and the pieces could be functionalized prior to assembly. The open cell nature of the foam would allow airflow through the material.

Yet another manufacturing process involves the fusion of two or more discrete pre-formed polystyrene parts. Through the application of highly localized high temperatures at or above the melting point of the material, it is possible to create a region where two or more pieces of polystyrene material would fuse together, e.g., by spot welding at discrete locations, or by seam welding along a continuous line. The welding method selected would be chosen to suite the final assembly, the tooling and the required robustness of the final part.

Finally, a matrix or unordered mesh of "noodle-like" strands of anion exchange material may be employed.

Design and Configuration Options for Air Capture Device a. Overview and Requirements The myriad of design options open for the matrix in terms of shapes and manufacturing processes lends itself to numerous configurations of the air capture device. These configurations provide opportunity for modularization, customization to fit existing spaces and optimization for cost, efficiency and productization.

b. Cubic Forms

The cubic form lends itself to efficient packing arrangements and modularization to support performance scale-up. An option is the development of a $CO_2$ capture system that is configured to fit into standard 20 and 40 foot shipping containers wherein the air capture device will be substantially in a cubic form.

The air capture device also could be comprised of numerous, discrete cubical modular sections that collectively provide the desired $CO_2$ capture performance. This provides an opportunity to individually regenerate each section, one at a time, allowing for continuous, uninterrupted $CO_2$ capture.

c. Circular Forms

The circular form lends itself to a design that mimics a conventional updraft cooling tower. The disc could be configured to be a "solid" form with uniform dimensions and features throughout its thickness. Airflow would follow a path parallel to the axis of rotation of the disc.

In one arrangement, the air capture disc may be oriented horizontally with a fan positioned above it to provide an updraft flow of air.

Another arrangement has the disc oriented vertically with the fan either in front or behind it. The disc may be arranged to slowly spin through a trough containing the chemicals to regenerate the active material.

In the retrofit market, the disc may be configured to fit within an existing updraft cooling tower thereby taking advantage of the available draft.

Another configuration of the circular form is one wherein the device has an annular cross section. In this configuration the processed air would move radially through the sides of the structure, either inwards or outwards depending on the installation.

d. Other Forms

There are many forms open to the design of the air capture device including those that are hollow. The configuration will be very much dependant on the constraints of the installation, notwithstanding those that govern performance as previously indicated.

e. Non-Uniform Cross-Section Forms

Adjustments to the cross section may be necessary in some instances to ensure uniform and efficient performance of the air capture device. This may lead to matrix configurations that have non-uniform cross sections and/or asymmetric profiles. Installation factors, enclosure designs and fan performance also may have a bearing on the final design and form of the matrix.

f. Matrix or Unordered Mesh Forms

Figure 2A:
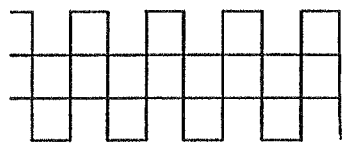
FIGS. 2a-2f are cross-sectional views schematically illustrating various configurations of air capture media in accordance with the present invention.
Figure 2B:
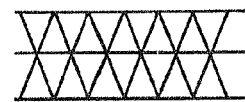
Figure 2C:
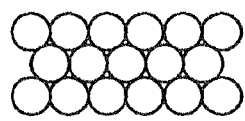
Figure 2D:
Figure 2E:
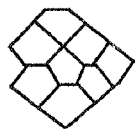
Figure 2F:
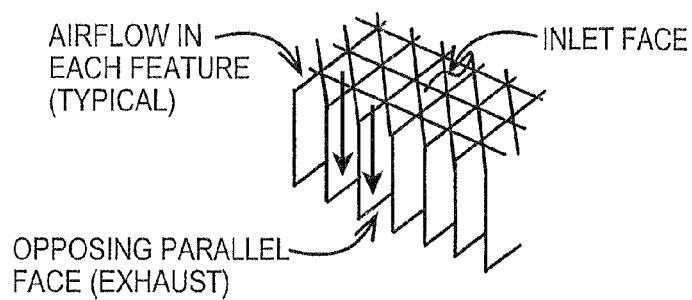
Figure 2G:
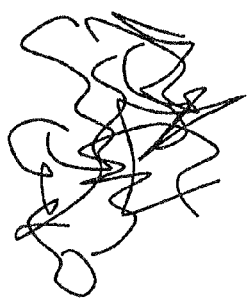
FIGS. 2g and 2h are perspective views illustrating "noodle-like" air capture media in accordance with the present invention.
Figure 2H:
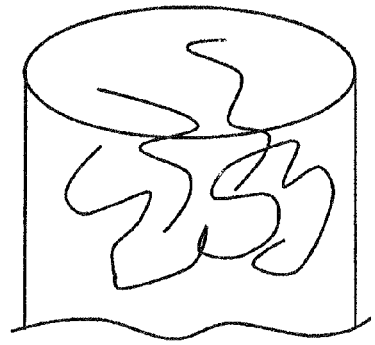

A matrix or unordered mesh of "noodle-like" strands 1 mm thick by 1 mm wide are formed by slitting sheets of 1 mm thick commercially available anion exchange material. The resulting "noodles" may then be loosely packed in a conduit, i.e., as shown in FIG. 2h, through which the air is directed.

Yet other structures that combine high surface area with low pressure drop advantageously may be employed in accordance with the present invention.

Figure 7:
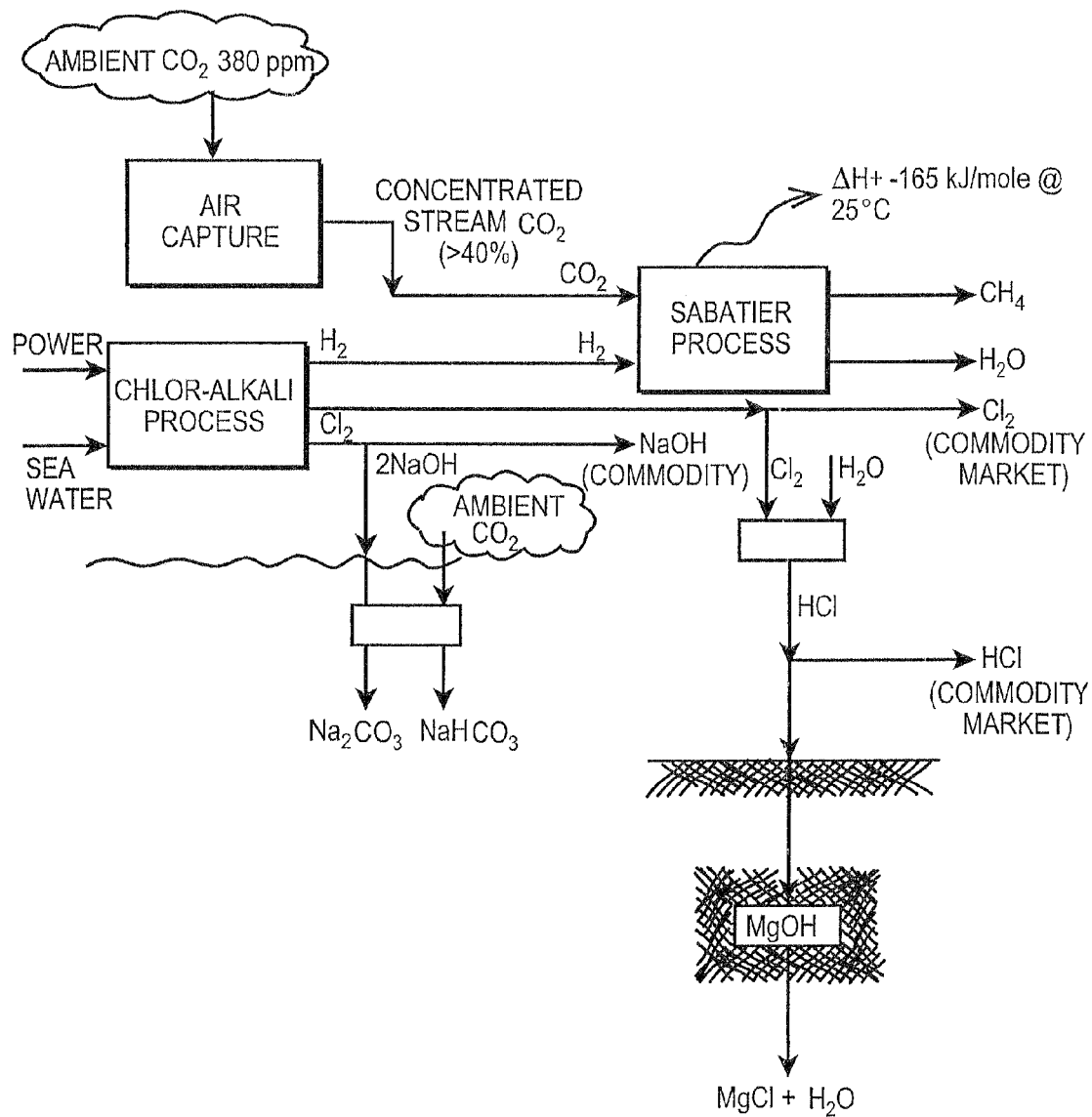
FIG. 7 is a schematic view illustrating $CO_2$ capture from the air followed by sequestration in accordance with a preferred embodiment of the invention.

In yet another aspect of the invention, the $CO_2$ captured from the air is permanently sequestered. There are several discrete processes that can be integrated to achieve permanent $CO_2$ sequestration. Referring to the attached drawing FIG. 7, two such processes are the air capture process such as described in our co-pending U.S. application Ser. No. 11/209, 962, filed Aug. 22, 2005, and a conventional industrial chlor-alkali process.

The chlor-alkali process is a common industrial process for the manufacture of commodity chlorine ($Cl_2$) and sodium hydroxide (NaOH) from NaCl by electrolysis, e.g., of sea water, in an electrolytic cell. The electrochemical current causes chloride ions to migrate to the anode where it is collected as chlorine gas. Sodium hydroxide and hydrogen also are formed. The overall process operates under the following stoichiometric relationship:

$$2H_2O+2NaCl \rightarrow 2NaOH+H_2+Cl_2 \Delta H=+543 \text{ kJ/g-mole } H_2 \qquad \text{I}$$

Typical uses for chlorine include a bleaching agent for the pulp and paper industry as well as a disinfectant agent. Sodium hydroxide is very common feed stack for numerous chemical and material manufacturing processes. The stream of hydrogen typically is considered a waste stream. Although some plants recover a portion of this waste stream for use as a heat and power fuel source, the majority produced worldwide is simply flared, i.e., burned in the atmosphere for disposal. The invention in one aspect leverages the product and waste streams from existing chlor-alkali processes as well as the $CO_2$ product stream from an air capture system by inserting a Sabatier reduction process, which is an exothermic process, downstream of the two previously mentioned processes. More particularly, in accordance with the present invention, the $CO_2$ collected in an air capture system, and the $H_2$ waste stream are combined over a nickel or ruthenium catalyst at an elevated temperature to reform these feed streams into $CH_4$ (methane) and $H_2O$ (water) under the stoichiometric conditions:

$$CO_2+4H_2 \rightarrow CH_4+2H_2O \Delta H=-165 \text{ kJ/mole @25}° \text{ C.} \qquad \text{II}$$

Thus, in accordance with one aspect of the present invention, carbon dioxide from an air capture system and hydrogen gas from a Chlor-alkali process are used as the feed streams for a Sabatier process. At low pressure (approximately 1 bar) and 400° C. to 600° C. operating temperature, a product stream of methane and water vapour evolves. To ensure the permanent sequestration of the carbon in the methane, the methane gas may become the feedstock for the plastics processing industry. The methane gas also may be burned as a synthetic fuel, or used as a feedstock for forming a liquid synthetic fuel.

Additional $CO_2$ sequestration can be achieved by further consolidation of the product streams of the chlor-alkali process. As above described, an $H_2$ stream is utilized to aid in the sequestration of $CO_2$ through the Sabatier process. An NaOH stream also may be utilized to capture and sequester $CO_2$. Specifically, NaOH is a strong solvent for $CO_2$. Thus, by exposing the NaOH to the atmosphere, atmospheric $CO_2$ will react with the NaOH to form stable carbonates according to the following reactions:

$$2NaOH+CO_2 \rightarrow Na_2CO_3+H_2O \text{ and,} \qquad \text{III}$$

$$NaOH+CO_2 \rightarrow NaHCO_3 \qquad \text{IV}$$

These compounds occur naturally in the environment especially in the oceans. Thus, once the NaOH has completely reacted with the $CO_2$ in the atmosphere, the resulting carbonates can be introduced into the ocean where they are complementary to the marine life, and may be used by the indigenous marine life to form such vital structures as hard coral and shells. Another possibility is the direct injection of NaOH into the ocean, changing the pH of the ocean which will allow the ocean to act as an atmospheric $CO_2$ collector as described in our aforesaid PCT Patent Application Serial No. PCT/US06/029,238.

The chlorine product stream may be safely sequestered in the earth, e.g., via its reaction with natural magnesium hydroxide (MgOH). The chlorine would be dissociated in water to produce hydrochloric acid which would react with the magnesium hydroxide producing magnesium chloride, which has various industrial uses, and water. Another possibility would be to leave the mineral salt in situ for permanent mineral sequestration.

Of course, the chlor-alkali product streams of NaOH, $Cl_2$ and HCl also are marketable commodities, and thus may be used for revenue generation as opposed to disposal.

Yet other possibilities include direct injection of $CO_2$ into deep wells or deep ocean storage.

The present invention generates carbon credits at several stages. One carbon credit results from removal of $CO_2$ from the air. An additional carbon credit results from sequestration of the carbon as sodium carbonate. Two carbon credits are earned by conversion of the carbon into sodium bicarbonate. An additional carbon credit also can be earned by acid injection of the carbon into minerals, i.e., to form salts, the $CO_2$ passed to deep well or deep ocean storage, or sequestration of the carbon into plastics methane or synthetic fuel.

Various changes are possible without departing from the spirit and scope of the invention. For example, NaOH has been described for reactivating the anionic exchange surface sorbent; however, the invention is not limited to the use of sodium hydroxide as a sorbent, and other sorbents capable of absorbing carbon dioxide, such as sodium carbonate may be used in the present invention. Also, while ion exchange material has been described as a preferred material for forming the backbone of the air capture device, other air capture devices such as described in our aforesaid PCT/US06/029238 and our PCT/US05/029979 advantageously may be employed. Also, rather than cut the "noodles" from anion exchange sheet material, threads of anionic exchange material may be formed by crushing anionic exchange resin material, and extruding the crushed resin material in a binder to form the "noodles" directly. Still other applications may be made without departing from the spirit and scope of the invention.

The invention claimed is:

1. A process for removing $CO_2$ from atmospheric air at a location remote from where the $CO_2$ was generated, comprising the steps of passing atmospheric air in contact with an apparatus comprising a solid anion exchange material, whereupon $CO_2$ is captured directly by the anion exchange material, and treating the anion exchange material to remove and concentrate the captured $CO_2$ and to convert the captured $CO_2$ to an useful product.

2. The process of claim 1, including the step of converting the captured $CO_2$ to methane.

3. The process of claim 2, wherein the captured $CO_2$ is converted to methane using a Sabatier process.

4. The process of claim 1, wherein the captured $CO_2$ is converted to liquid synthetic fuel or a plastic.

5. A process for removing $CO_2$ from atmospheric air at a location remote from where the $CO_2$ was generated, comprising the steps of passing atmospheric air in contact with an apparatus comprising a solid anion exchange material, whereupon $CO_2$ is captured directly by anion exchange material, and treating the anion exchange material to remove and concentrate the captured $CO_2$, and permanently removing the captured $CO_2$ from the atmosphere by passing the captured $CO_2$ to deep well or deep ocean storage.

6. The process of claim 1, wherein the solid anion exchange material is in the form of a matrix.

7. The process of claim 5, wherein the solid anion exchange material is in the form of a matrix.

* * * * *